United States Patent [19]

Cozzi et al.

[11] 4,267,327

[45] May 12, 1981

[54] 2-HYDROXYMETHYL-PYRAZINE DERIVATIVES AND PROCESS FOR THEIR PREPARATION

[75] Inventors: Paolo Cozzi, Milan; Osvaldo Magni, Certosa di Pavia; Leone Bertone, Milan; Romano Angelucci, Milan; Pier P. Lovisolo, Milan, all of Italy

[73] Assignee: Farmitalia Carlo Erba S.p.A., Milan, Italy

[21] Appl. No.: 15,223

[22] Filed: Feb. 26, 1979

[30] Foreign Application Priority Data

Mar. 23, 1978 [IT] Italy ............................... 21520 A/78

[51] Int. Cl.³ .......................................... C07D 241/52

[52] U.S. Cl. ..................................... 544/336; 424/250

[58] Field of Search .......................................... 544/336

[56] References Cited

U.S. PATENT DOCUMENTS 4,051,245   9/1977   Ambrogi et al. .................... 424/250

Primary Examiner—Jose Tovar
Attorney, Agent, or Firm—Murray and Whisenhunt

[57] ABSTRACT

2-Hydroxymethyl-pyrazine derivatives are disclosed, such as, for instance, the compound 2-hydroxymethyl-5-methylpyrazine-4-oxide. The compounds exhibit an elevated lipid lowering activity, and can be used to control triglyceride and cholesterol levels.

2 Claims, No Drawings

2-HYDROXYMETHYL-PYRAZINE DERIVATIVES AND PROCESS FOR THEIR PREPARATION

The present invention relates to 2-hydroxymethyl-pyrazine derivatives, a process for their preparation and pharmaceutical compositions containing them. One object of the invention is represented by compounds of the general formula (I)

$$
\begin{array}{c}
(O)_n \\
\uparrow \\
R_2 \diagdown N \diagup R_1 \\
R_3 \diagup N \diagdown CH_2OR_4
\end{array}
\quad (I)
$$

wherein
n is zero or 1;
the groups $R_1$, $R_2$ and $R_3$, which can be identical or different, each is hydrogen, $C_1$–$C_6$ alkyl, $C_1$–$C_6$ alkoxy, hydroxy, halogen, mercapto, amino, $C_2$–$C_6$ acylamino;
$R_4$ is hydrogen or the radical $$-\underset{\underset{O}{\|}}{C}-R_5,$$

wherein $R_5$ is $C_2$–$C_6$ alkyl, $C_2$–$C_6$ alkenyl, $C_3$–$C_8$ cycloalkyl, unsubstituted or substituted by one or more substituents selected from the group consisting of $C_1$–$C_6$ alkyl, $C_1$–$C_6$ alkoxy, halogen, hydroxy, amino;
with the provision that: (a) when n is zero, $R_1$ being $=R_2=R_3=$hydrogen or $R_1=R_2=R_3=$methyl or $R_1=R_3=$hydrogen and $R_2=$methyl or $R_1=R_2=$hydrogen and $R_3=$methyl, $R_4$ is different from hydrogen;
(b) when n is 1, $R_1$ being$=R_2=R_3=$methyl, $R_4$ is different from hydrogen.

Another object of the invention is represented by pharmaceutical compositions containing compounds having the formula (I) given above wherein n is zero or 1; the groups $R_1$, $R_2$ and $R_3$, which can be identical or different, each is hydrogen, $C_1$–$C_6$ alkyl, $C_1$–$C_6$ alkoxy, hydroxy, halogen, mercapto, amino, $C_2$–$C_6$ acylamino; $R_4$ is hydrogen or the radical $$-\underset{\underset{O}{\|}}{C}-R_5',$$

wherein $R_5'$ is $C_1$–$C_6$ alkyl, $C_2$–$C_6$ alkenyl, $C_3$–$C_8$ cycloalkyl unsubstituted or substituted by one or more substituents selected from the group consisting of $C_1$–$C_6$ alkyl, $C_1$–$C_6$ alkoxy, halogen, hydroxy, amino. The salts of the above compounds with pharmaceutically acceptable (i.e. nontoxic) acids are also included in the subject matter of the invention, as also the pharmaceutical compositions containing said salts.

Examples of pharmaceutically acceptable acids are both inorganic acids, such as for example hydrochloric, hydrobromic, sulphuric, phosphoric and nitric acid, and organic acids such as for example citric, tartaric, fumaric, maleic, malic, mandelic and methanesulphonic acid. The alkyl, alkoxy, alkenyl groups can be straight- or branched-chain.

A $C_1$–$C_6$ alkyl group is preferably methyl, ethyl, propyl.

A $C_2$–$C_6$ alkyl group is preferably ethyl, propyl, isopropyl, tert-butyl.

A $C_1$–$C_6$ alkoxy group is preferably methoxy, ethoxy, propoxy.

A $C_2$–$C_6$ alkenyl group is preferably vinyl or allyl.

A $C_3$–$C_8$ cycloalkyl group is preferably cyclopentyl, cyclohexyl, cycloheptyl.

In a $C_2$–$C_6$ acylamino group the acyl group is preferably $C_2$–$C_6$ alkanoyl, in particular acetyl and propionyl. A halogen is preferably chlorine, bromine, fluorine.

Preferred compounds of the invention are the compounds of formula (I) wherein n is 1.

The novel compounds of the invention can be prepared by the reduction of a compound of formula (II)

$$
\begin{array}{c}
(O)_n \\
\uparrow \\
R_2 \diagdown N \diagup R_1 \\
R_3 \diagup N \diagdown X
\end{array}
\quad (II)
$$

wherein
n, $R_1$, $R_2$, $R_3$ have all the meanings stated above and X represents a free carboxyl group, salified or esterified, in this way obtaining a compound of formula (I) wherein $R_4$ is hydrogen and, if desired, by reaction of a compound of formula (I) wherein $R_4$ is hydrogen or a reactive derivative thereof, with an acid of formula (III)

$$R_5\text{-COOH} \quad (III)$$

wherein
$R_5$ has the meanings stated above, or with a reactive derivative thereof and/or, if desired, by conversion of a compound of formula (I) into another compound of formula (I) and/or, if desired, by salification of a compound of formula (I).

When X is a salified carboxyl group, the salt is preferably an alkali metal salt, but can also be a salt of other metals, as also a salt with organic amines, for example triethylamine, piperidine, morpholine, pyrrolidine.

When X is an esterified carboxyl group, the ester can be an alkyl ester, an alkenyl, cycloalkyl, cycloalkenyl, cycloalkylalkyl, cycloalkenylalkyl ester, wherein, for example, the aliphatic and cycloaliphatic radical contain from 1 to 12 carbon atoms in the chain or from 3 to 8 carbon atoms in the ring, as also an aryl or aralkyl ester wherein the aryl is preferably phenyl, substituted or unsubstituted, a hydroxyalkyl, alkoxyalkyl or cycloalkoxyalkyl ester, wherein the cycloalkyl radical contains from 3 to 8 carbon atoms in the ring, or a tert-amino-$C_1$–$C_6$ alkylester. The ester is preferably an alkyl ester. Reactive derivatives of a compound of formula (I) wherein $R_4$ is hydrogen are for example the alkoxide, for example alkaline, especially of sodium or potassium, or an active ester, for example the methanesulphonate and the p-toluenesulphonate.

An active derivative of an acid of formula (III) is for example an acidic halide, for example the acidic chloride, the anhydride or a mixed anhydride, which can for instance be prepared by reaction of ethyl chloroformate or pivaloyl chloride with a salt of the acid of formula (III), for example a salt with a tertiary aliphatic amine.

The reduction of a compound of formula (II) wherein X is an esterified carboxyl can for example be carried out using sodium borohydride in a solvent such as for example methanol, ethanol, isopropanol or in mixture of one of these solvents with water in ratios which vary depending on the solubility of the starting product; the said reduction can also be performed e.g. using aluminium lithium hydride in inert solvents such as for example anhydrous ethyl ether or anhydrous tetrahydrofuran at temperatures which in both cases range from approximately 0° C. to the solvent reflux temperature, for reaction times of between approximately 30 minutes and approximately 24 hours.

The reduction of a compound of formula (II) wherein X represents a free carboxyl group is preferably carried out using aluminium lithium hydride in inert solvents such as for example anhydrous ethyl ether, anhydrous diethylene glycol dimethyl ether, anhydrous tetrahydrofuran or mixtures thereof or else using preformed solutions of boron hydride in the aforesaid anhydrous solvents, or boron hydride prepared in situ in the reaction means from sodium borohydride and boron trifluoride etherate, preferably in diethylene glycol dimethyl ether, at temperatures ranging from 0° C. to the solvent reflux temperature, for reaction times of between approximately 30 minutes and 12 hours.

The reduction of a compound of formula (II) wherein X represents a salified carboxyl group is preferably carried out in conditions analogous to those employed in the reduction of a compound of formula (II) wherein X is a free carboxyl.

The reaction between a compound of formula (I) wherein $R_4$ is hydrogen and an acid of formula (III) so as to obtain a compound of formula (I) wherein $R_4$ is a

group wherein $R_5$ is defined as above is preferably carried out in an inert solvent, for example benzene, toluene, xylene, preferably in the presence of an acid, such as for example hydrochloric acid, sulphuric acid, p-toluenesulphonic acid monohydrate, or in the presence of a Lewis acid for example boron trifluoride etherate or in the presence of a condensing agent, such as for example N,N'-dicyclohexylcarbodiimide, at temperatures ranging from between approximately 60° C. and the reflux temperature, for reaction times which may vary between 2 and 36 hours approximately, with elimination when necessary of the water which is liberated during the reaction by means of azeotropic distillation. When the reactive derivative of the acid of formula (III) is the acidic chloride, the reaction with the compound of formula (I) wherein $R_4$ is hydrogen is preferably carried out in a basic environment, for example directly in pyridine, or in an inert solvent such as for example benzene, toluene, xylene, in the presence of a tertiary base, for example triethylamine or piperidine. When the reactive derivative of the acid of formula (III) is its anhydride or a mixed anhydride, the reaction with the compound of formula (I) wherein $R_4$ is hydrogen, can be carried out in one of the aforesaid inert solvents or in the absence of solvent, if necessary in the presence of a catalyst such as for example sulphuric acid or zinc chloride. When the reactive derivative of a compound of formula (I) wherein $R_4$ is hydrogen is one of its alkoxides, for example an alkaline alkoxide, e.g. of sodium or potassium, it is preferably reacted with a reactive derivative of a compound of formula (III), preferably with the halide, for example the acidic chloride, or with the anhydride, in a solvent such as for example chloroform, benzene, toluene, dimethylformamide or pyridine, at the solvent reflux temperature, for times ranging from 1 to 24 hours approximately. When the reactive derivative of a compound of formula (I) wherein $R_4$ is hydrogen is an active ester thereof, such as for example the methanesulphonate or the p-toluenesulphonate, it is preferably reacted with the acid of formula (III) or with a salt thereof without solvent or in an inert solvent such as for example benzene, totluene, xylene, dimethylformamide, if necessary in the presence of a base, e.g. pyridine, triethylamine, an alkali or alkaline earth carbonate or bicarbonate, at the reflux temperature, for periods ranging from 2 to 24 hours approximately.

Both the optional conversion of a compound of formula (I) into another compound of formula (I) and the optional salification are carried out with conventional methods. Thus for example a compound of formula (I) wherein $R_4$ is hydrogen and $R_1$ and/or $R_2$ and/or $R_3$ are hydroxy, can be obtained from the corresponding compound of formula (I) wherein $R_4$ is hydrogen, $R_1$ and/or $R_2$ and/or $R_3$ are halogen, for example chlorine or bromine, by treatment with a base, for example aqueous sodium or potassium hydroxide at the reflux temperature and for times ranging from 1 to 4 hours. A compound of formula (I) wherein $R_4$ is hydrogen and $R_1$ and/or $R_2$ and/or $R_3$ are hydroxy can also be prepared from a compound of formula (I) wherein $R_4$ is hydrogen and $R_1$ and/or $R_2$ and/or $R_3$ are $C_1$–$C_6$ alkoxy by deetherification which can for example be performed by acid cleavage, preferably by effect of a hydrohalic acid such as for example hydrochloric or hydroiodic acid, at a temperature of between approximately 60° C. and the reflux temperature and for times of between approximately 1 hour and approximately 8 hours. The deetherification can also be performed by effect of a salt of pyridine, for example pyridine hydrochloride or by effect of a Lewis acid like $BBr_3$.

A compound of formula (I) wherein $R_4$ has all the meanings stated above, $R_1$ and/or $R_2$ and/or $R_3$ are hydroxy, can be obtained from a compound of formula (I) wherein $R_4$ has all the meanings stated above, $R_1$ and/or $R_2$ and/or $R_3$ are amino by diazotization, for example effected with sodium nitrite in sulphuric acid, at a temperature ranging from approximately 0° C. to approximately 5° C. and by subsequent decomposition of the diazonium salt which forms; such decomposition occurs for example by heating at a temperature of between approximately 20° C. and approximately 100° C., for times ranging from approximately 15 minutes to approximately 3 hours.

A compound of formula (I) wherein $R_4$ has all the meanings stated above and $R_1$ and/or $R_2$ and/or $R_3$ represent $C_1$–$C_6$ alkoxy, can be prepared from a compound of formula (I) wherein $R_4$ has all the meanings stated above, $R_1$ and/or $R_2$ and/or $R_3$ are halogen, preferably chlorine, by treatment for example with alkaline alkoxide, for example of sodium or potassium, at a temperature ranging from approximately 0° C. to the reflux temperature of the alcohol used as solvent, for times of between approximately 20 minutes and approximately 8 hours.

A compound of formula (I) wherein R₄ has all the meanings stated above, R₁ and/or R₂ and/or R₃ are mercapto, can be prepared by reaction of a compound of formula (I) wherein R₄ has all the meanings stated above and R₁ and/or R₂ and/or R₃ are halogen, in particular bromine, with an alkaline hydrosulphide, preferably sodium or potassium hydrosulphide, in a suitable solvent such as for example dimethylformamide, at a temperature of between approximately 20° C. and the reflux temperature, for times ranging from approximately 1 hour to approximately 8 hours.

A compound of formula (I) wherein R₁ and/or R₂ and/or R₃ are C₂-C₆ acylamino and R₄ is different from hydrogen can be prepared starting from a compound of formula (I) wherein R₁ and/or R₂ and/or R₃ are amino and R₄ is different from hydrogen, by acylation, for example by treatment with an anhydride or a halide, preferably the chloride of an acid of formula R₆-COOH, wherein R₆ is C₁-C₅ alkyl. A compound of formula (I) wherein n is zero, R₄ is different from hydrogen and the groups R₁, R₂ and R₃ each have all the meanings stated above except for hydroxy and mercapto, can be converted into a compound of formula (I) wherein n is 1, R₄ is different from hydrogen and each of the groups R₁, R₂ and R₃ has all the meanings stated above, except for hydroxy and mercapto, by oxidation.

The oxidation is preferably carried out by means of organic peracids prepared in situ by effect of hydrogen peroxide, for example 30% w/v, on suitable organic acids.

Examples of preferred peracids are peracetic acid, m-chloroperbenzoic acid, permaleic acid and monoperphthalic acid.

The oxidation reaction is preferably carried out at temperatures ranging between approximately 20° C. and the reflux temperature, for reaction times of between 1 and 24 hours approximately.

The compounds of formula (I) wherein n is zero or 1, R₁, R₂ and R₃ have all the meanings initially stated above and R₄ is the radical

wherein R'₅ is methyl, are known compounds. The compounds of formula (I) wherein n is zero, R₁=R₂=R₃=R₄=hydrogen or R₁=R₂=R₄=hydrogen and R₃=methyl or R₁=R₃=R₄=hydrogen and R₂=methyl, and the compounds of formula (I) wherein n is zero or 1, R₄ is hydrogen and R₁=R₂=R₃=methyl, are also known compounds.

The aforementioned known compounds are described in literature for example in J. Org. Chem. 26, 126 (1961) and in J. Am. Chem. Soc., 81, 5160 (1959) where there is not however reported any reference to a possible therapeutic use or to a possible pharmaceutical dosage form containing the said compounds. The known compounds can be prepared with known methods, for example those described in the aforesaid references, or with the method described in the present application for the preparation of the novel compounds of the invention.

The starting materials are known, or can be respectively prepared with known methods.

For example the compounds of formula (II) wherein n is zero, R₁ is methyl, R₂ and R₃ are hydrogen and X is carboxy or carbomethoxy are described in J. Med. Chem. 13, 77 (1970). The compounds of formula (II) wherein n is zero, R₁ is halogen, R₂ and R₃ are hydrogen and X is carboxy are described in J. Am. Chem. Soc. 71, 2798 (1949) and in J. Chem. Soc. 1955, 1379. The compound of formula (II) wherein n is zero, R₁ is amino, R₂ and R₃ are hydrogen and X is carboxy is described in J. Am. Chem. Soc. 67, 802 (1945); the compound of formula (II) wherein n is zero, R₁ is hydroxy, R₂ and R₃ are hydrogen and X is carboxy is described in J. Am. Chem. Soc. 70, 3911 (1948); the compound of formula (I) wherein n is zero, R₁ is mercapto, R₂ and R₃ are hydrogen and X is carboxy is described in J. Med. Chem. 12, 285 (1969); the compound of formula (II) wherein n is zero, R₁ is methoxy, R₂ and R₃ are hydrogen and X is carboxy is described in Chem. Pharm. Bull. 20(10),2204 (1972).

The compound of formula (II) wherein n is zero, R₂ is methyl, R₁ and R₃ are hydrogen and X is carboxy is described in Chem. Ber. 99, 364 (1966).

The compounds of formula (II) wherein n is zero, R₂ is amino or hydroxy, R₁ and R₃ are hydrogen and X is carboxy or carbomethoxy are described in Helv. Chim. Acta. 47, 873 (1964). The compound of formula (II) wherein n is zero, R₃ is methyl, X is carboxy and R₁ and R₂ are hydrogen is described in J. Am. Chem. Soc. 74, 3617 (1952). The compounds of formula (II) wherein n is zero, R₃ is halogen or methoxy, R₁ and R₂ are hydrogen and X is carboxy are described in Chem. Pharm. Bull. 19, 1337 (1971) and in Arzneim. Forsch. 21, 200 (1971). The compound of formula (II) wherein n is zero, R₃ is amino, R₁ and R₂ are hydrogen and X is carboxy is described in J. Org. Chem. 24, 345 (1959); the compound of formula (II) wherein n is zero, R₃ is hydroxy, R₁ and R₂ are hydrogen and X is carboxy is described in Acta. Pol. Pharm. 23, 411 (1966). The compounds of formula (II) wherein n is zero, R₂ is halogen or C₁-C₆ alkoxy, R₁ and R₃ are hydrogen and X is carboxy are also prepared in known manner.

For example the compound 2-carboxy-5-chloro-pyrazine can be prepared by treating with an excess of phosphorus oxychloride, at the reflux temperature, the 2-carboxy-5-hydroxy-pyrazine compound in its turn obtained in the manner described in Helv. Chim. Acta 47, 873 (1964).

Similarly the compound 2-carboxy-5-bromo-pyrazine can be obtained from the 2-carboxy-5-hydroxy-pyrazine compound by treating under heating with an excess of phosphoryl bromide. The compound 2-carboxy-5-fluoro-pyrazine can be prepared starting from the 2-carboxy-5-amino-pyrazine compound described in Helv. Chim. Acta 47, 873 (1964) by means of a modification of the known Schieman reaction.

The compounds of formula (II) wherein n is zero, R₁ and/or R₂ and/or R₃ are C₁-C₆ alkoxy and X is carboxy can be obtained by treatment of the corresponding compounds in which R₁ and/or R₂ and/or R₃ are halogen, for example chlorine, with an alkoxide, preferably alkaline, for example sodium methoxide in methanol at reflux temperature.

The compounds of formula (II) wherein n is 1, are also known and obtainable by means of known methods.

For example the compounds of formula (II) wherein n is 1, R₁, R₂ and R₃ are hydrogen and X is carboxy or carbalkoxy are described in Acta Pol. Pharm. 21(5), 429 (1964). The compounds of formula (II) wherein n is 1, R₁ and/or R₂ and/or R₃ are C₁-C₆ alkyl and X is carboxy or carbalkoxy can be prepared as described in the British Pat. No. 1.361.967, that is to say by oxidation of the corresponding compounds wherein n is zero, with peracids, for example those indicated above.

Also the compounds of formula (II) wherein n is 1 and $R_1$, $R_2$ and $R_3$ have the other meanings stated above except hydroxy and mercapto, can be prepared from the corresponding compounds of formula (II) wherein n is zero, by oxidation with peracids as stated above.

The compounds of formula (II) wherein n is 1, $R_1$ and/or $R_2$ and/or $R_3$ are hydroxy or mercapto respectively, can be for example prepared starting from the corresponding compounds of formula (II) wherein n is 1 and $R_1$ and/or $R_2$ and/or $R_3$ are amino or respectively halogen, in the reaction conditions stated above in connection with the optional conversion of a compound of formula (I) wherein $R_1$ and/or $R_2$ and/or $R_3$ are amino into a compound of formula (I) wherein $R_1$ and/or $R_2$ and/or $R_3$ are hydroxy, and, respectively, in connection with the optional conversion of a compound of formula (I) wherein $R_1$ and/or $R_2$ and/or $R_3$ are halogen into a compound of formula (I) wherein $R_1$ and/or $R_2$ and/or $R_3$ are mercapto.

A compound of formula (II) wherein n is 1, each of $R_1$, $R_2$ and $R_3$ can have the meanings stated above and X is a carboxyl group salified or esterified, can also be obtained with known methods, for example by salification or esterification of a compound of formula (II) wherein X is carboxy. The compounds of formula (III) are known and can be prepared with known methods.

The compounds of the present invention possess an elevated lipid lowering activity, in particular anti-lipolytic and, further, triglyceride and cholesterol lowering activity.

The activity of the compounds of the invention was evaluated on groups of six ICEM:CER (SPF Caw) rats, fasted—but not deprived of water—for 18 hours, of average weight 180 g. The compounds being examined were suspended in methocel (0.5% in distilled water) and administered by stomach tube at the doses of 3.125 mg/kg, 12.5 mg/kg and 50 mg/kg, each dose being contained in a volume of 0.5 ml per 100 g of rat body weight.

The animals were killed at 60, 120 and 240 minutes after treatment. One group of animals was treated with the 50 mg/kg dose and sacrificed 480 minutes after treatment.

A group of six animals treated with the suspending agent only (control group) were available for each sampling time. At the times indicated sacrifice of the animals took place by means of decapitation, the blood being immediately cooled and centrifuged. The following variables were determined on the plasma:

(1) free fatty acids [F F A] with the method of Dole as modified by Trout (Dole V. P., Clin. Invest., 35, 150, 1956; Trout D. L., J. Lip. Rs., 1, 199, 1960), at 60, 120 and 240 minutes;

(2) triglycerides (TG) with the method of Mendez (Mendez J., Clin. Chem., 21, N. 6, 768, 1975), at 60, 120 and 240 minutes.

(3) total cholesterol with the method of Abell (Abell L. L., J. Biol. Chem., 195, 357, 1952) at 480 minutes.

On the TG levels thus determined calculation was made, by means of statistical analyses, of the mean and the standard error, and analysis of variance and Dunnet's test were effected.

On the total cholesterol values the mean and the standard error were calculated, and Student's test applied. The Tables that follow report, as exemplification, the F.F.A., TG and total cholesterol values in animals treated with one of the compounds of the invention, identified by the coding K 10603, in comparison with the values of the same parameters in non-treated animals.

TABLE 1

Values of free fatty acids expressed in μmol/100 ml of plasma and values of triglycerides expressed in mg/100 of plasma.
Mean and S.E. and Dunnet's test at 60′, 120′ and 240′ minutes (HS = highly significant; NS = not significant)

| Time | Control | K 10603 3.125 mg/kg/os | K 10603 12.5 mg/kg/os | K 10603 50 mg/kg/os | COMPARISONS | Results | |
|---|---|---|---|---|---|---|---|
| 60′ | 73,7 ± 4,3 | 20,3 ± 3,7 | 15,5 ± 1,6 | 13,5 ± 0,5 | Controls → K 10603 3,125 mg/kg/os | HS | free fatty acids |
| | | | | | Controls → K 10603 12,5 mg/kg/os | HS | |
| | | | | | Controls → K 10603 50 mg/kg/os | HS | |
| 120′ | 70,2 ± 4,2 | 65,5 ± 4,9 | 32,8 ± 3,3 | 17,3 ± 2,6 | Controls → K 10603 3,125 mg/kg/os | NS | |
| | | | | | Controls → K 10603 12,5 mg/kg/os | HS | |
| | | | | | Controls → K 10603 50 mg/kg/os | HS | |
| 240′ | 75,7 ± 4,5 | 90,0 ± 5,4 | 84.1 ± 2,4 | 37,8 ± 4,5 | Controls → K 10603 3,125 mg/kg/os | NS | |
| | | | | | Controls→ K 10603 12,5 mg/kg/os | NS | |
| | | | | | Controls → K 10603 50 mg/kg/os | HS | |
| 60′ | 77,3 ± 7,3 | 13,8 ± 2,0 | 23,5 ± 1,2 | 18,3 ± 3,9 | Controls → K 10603 3,125 mg/kg/os | HS | Triglycerides |
| | | | | | Controls → K 10603 12,5 mg/kg/os | HS | |
| | | | | | Controls → K 10603 50 mg/kg/os | HS | |
| 120′ | 52,8 ± 6,8 | 27,0 ± 3,4 | 17,8 ± 5,2 | 16,8 ± 4,3 | Controls → K 10603 3,125 mg/kg/os | HS | |
| | | | | | Controls → K 10603 12,5 mg/kg/os | HS | |
| | | | | | Controls → K 10603 50 mg/kg/os | HS | |
| 240′ | 56,3 ± 9,6 | 38,7 ± 3,8 | 25,5 ± 3,3 | 6,7 ± 1,5 | Controls → K 10603 3,125 mg/kg/os | NS | |
| | | | | | Controls → K 10603 12,5 mg/kg/os | HS | |
| | | | | | Controls → K 10603 50 mg/kg/os | HS | |

K 10603 = 2-hydroxymethyl-5-methyl-pyrazine-4-oxide

TABLE 2

Total cholesterol values expressed as mg/100ml of plasma at 480 minutes - Mean and standard error and Student's t test (HS = highly significant).

| Control | K 10603 50 mg/kg/os | Result |
|---|---|---|
| 86.7 ± 2.6 | 68.7 ± 2.1 | HS |

K 10603 = 2-hydroxymethyl-5-methyl-pyrazine-4-oxide.

An examination of Table 1 shows clearly that K 10603 exerts a distinct anti-lipolytic effect, even at low dosage, for example 3.125 mg/kg/os at 60 minutes. The "rebound" effect when the activity of the product ceases is slight only; in fact, although in the groups treated with 3.125 mg/kg and with 12.5 mg/kg there were, at 240 minutes, higher free fatty acid values than in the control animals, the difference is not significant. The triglyceride regulating activity is pronounced in all the treated groups, with one only exception in the case of the 3.125 mg/kg dose at 240 minutes.

It can be seen from Table 2 that the substance examined exerts a significant cholesterol regulating effect, at the maximum dose of 50 mg/kg/os, 8 hours after treatment.

As already stated, the pharmaceutical compositions containing compounds of the general formula (I) wherein n, $R_1$, $R_2$, $R_3$ and $R_4$ have all the meanings initially reported, without any limitation whatsoever, or their salts, also constitute subject matter of the present invention.

The said pharmaceutical compositions contain the compounds of the invention and a pharmaceutically acceptable carrier and/or a pharmaceutically acceptable diluent.

Pharmaceutically acceptable carriers and/or diluents, are for example gelatin capsules, microcrystalline cellulose, lactose, natural gums, starches, such as for example corn starch and potato starch, cellulose derivatives such as for example sodium carboxymethyl cellulose, ethyl cellulose, methyl cellulose, cellulose acetate or phthalate, gelatin, talc, stearic acid, magnesium stearate, as also the other pharmaceutically acceptable substances employed in pharmaceutical compositions.

The compositions may be for example in a form suitable for oral administration, for example tablets, capsules, sugar or film coated tablets, liquid solutions or suspensions, but may also be administered by injection or rectally. The dosage adapted for oral administration in adults for example ranges from approximately 100 mg to approximately 500 mg, preferably 200 mg per dose, for example 1-4 times daily.

The toxicity of the compounds of the invention is negligible. For example, for the compound cited in the Tables given above the orientative acute toxicity ($LD_{50}$) in the mouse, determined with single administration of increasing doses and measured on the seventh day after the treatment was, by mouth, higher than 800 mg/kg. Similar $LD_{50}$ values are found for all the other compounds of the invention.

The I.R. spectrum of the compounds was measured in solid phase (KBr) or in Nujol solution or in a solution of a suitable solvent such as $CHCl_3$, using a Perkin-Elmer 125 spectrophotometer.

The N.M.R. spectrum was measured preferably in solution of dimethyl sulphoxide-$d_6$ or of $CDCl_3$, using a 90 M-hertz Bruker HFX apparatus.

The $R_f$ values were determined by thin layer chromatography on ready-to-use silica gel plates of 0.25-mm coating thickness. The following examples illustrate but do not limit the invention.

EXAMPLE 1

Method A—To a solution of 2-carbomethoxy-5-methyl-pyrazine-4-oxide (6.3 g) in a mixture of water (50 ml) and methyl alcohol (25 ml) cooled to a temperature comprised between 0° C. and 5° C., addition was made in portions, under stirring and maintaining the temperature below 10° C., of sodium borohydride (4.25 g). The reaction mixture was stirred for 2 hours at room temperature, the solvent then evaporated under vacuum and the residue extracted several times with methanol under heating. After it had been evaporated to dryness, the methanolic solution was taken up with $CHCl_3$ and filtered.

By first dehydrating the chloroform extracts and then evaporating to dryness there was obtained 4 g (76%) of 2-hydroxymethyl-5-methyl-pyrazine-4-oxide, melting range 110°–111° C.

Analysis: Found: C, 51.37; H, 5.76; N, 19.94; Calc'd for $C_6H_8N_2O_2$: C, 51.42; H, 5.75; N, 19.99 T.L.C.: mobile phase: $CHCl_3:CH_3OH = 170:30$ $R_f=0.38$.

N.M.R.($CDCl_3$)$\delta$ ppm 2.42 3H s, 4.36 1H broad band, 4.74 2H s, 8.3 1H s, 8.38 1H s.

The 2-carbomethoxy-5-methyl-pyrazine-4-oxide used as starting material was prepared, with yield of 83%, from 5-methyl-2-pyrazinoic-4-oxide refluxed for twelve hours in anhydrous methanol in the presence of boron trifluoride etherate, melting range 146°–148° C.

Analysis: Found: C, 49.91; H, 4.82; N, 16.58: Calc'd for $C_7H_8N_2O_3$: C, 50.00; H, 4.80; N, 16.65: T.L.C. mobile phase: $CHCl_3:CH_3OH:NH_2OH = 190:10:0.5$ $R_f=0.61$.

The following compounds were similarly obtained:
2-hydroxymethyl-pyrazine-4-oxide;
2-hydroxymethyl-5-methoxy-pyrazine-4-oxide;
2-hydroxymethyl-3-amino-pyrazine-4-oxide;
2-hydroxymethyl-5-amino-pyrazine-4-oxide;
2-hydroxymethyl-6-amino-pyrazine-4-oxide;
2-hydroxymethyl-6-methyl-pyrazine-4-oxide;
2-hydroxymethyl-5,6-dimethyl-pyrazine-4-oxide;

From the corresponding pyrazines not oxidated in position 4, the following compounds were obtained similarly:
2-hydroxymethyl-5-methoxy-pyrazine;
2-hydroxymethyl-5-amino-pyrazine;
2-hydroxymethyl-6-amino-pyrazine.

Method B—To a solution of 2-carboxy-5-methyl-pyrazine-4-oxide (1.5 g) in diethylene glycol dimethyl ether (80 ml) addition was made at 0° C. under an atmosphere of nitrogen of a solution (1 M) of diborane in tetrahydrofuran (30 ml). To the reaction mixture maintained for 3 hours at 0° C. and 1 hour at room temperature, cautious addition was made of ethanol (50 ml) and then of a 0.5 M solution of alcoholic potash (25 ml). The resultant solution after evaporation at reduced pressure was taken up with chloroform which, on evaporation to dryness, gave 1.2 g of 2-hydroxymethyl-5-methyl-pyrazine-4-oxide.

The following compounds were prepared similarly:
2-hydroxymethyl-5-fluoro-pyrazine-4-oxide;
2-hydroxymethyl-5-chloro-pyrazine-4-oxide;
2-hydroxymethyl-6-chloro-pyrazine-4-oxide;
2-hydroxymethyl-5-bromo-pyrazine-4-oxide.

From the corresponding pyrazines not oxidated in position 4, the following compounds were similarly prepared:
2-hydroxymethyl-5-fluoro-pyrazine;
2-hydroxymethyl-5-chloro-pyrazine;
2-hydroxymethyl-5-bromo-pyrazine.

EXAMPLE 2

2-hydroxymethyl-5-hydroxy-pyrazine-4-oxide

A suspension of 2-hydroxymethyl-5-chloro-pyrazine-4-oxide (1.6 g) in 10% NaOH (15 ml) was maintained at boiling for two hours. The reaction mixture was evaporated to dryness and the residue dissolved in water (10 ml). On acidification of the resultant solution with 10% HCl a precipitate was produced which was filtered and washed with a little ice-water, obtaining 1 g (70%) of 2-hydroxymethyl-5-hydroxy-pyrazine-4-oxide.

The following compounds were similarly prepared:
2-hydroxymethyl-6-hydroxy-pyrazine-4-oxide;
2-hydroxymethyl-3-hydroxy-pyrazine-4-oxide.

EXAMPLE 3

5-methyl-2-pyrazinylmethyl pivalate

To a solution of 2-hydroxymethyl-5-methylpyrazine (6.2 g) and triethylamine (6.4 ml) in anhydrous benzene (150 ml) dropwise addition was made of a solution of pivaloyl chloride (6.15 ml) in anhydrous benzene (50 ml). The solution was maintained at boiling for 7 hours, the solvent was then evaporated and the residue treated with acetone. After filtration of the insoluble solid, the filtrate was evaporated to dryness and the residue redissolved in chloroform. The chloroform solution was first dehydrated and then evaporated to dryness, obtaining 7 g (71.5%) of 5-methyl-2-pyrazinylmethyl pivalate, b.p.=74° C./0.1 mmHg.

The following compounds were similarly obtained:
2-pyrazinylmethyl pivalate;
5-fluoro-2-pyrazinylmethyl pivalate;
5-chloro-2-pyrazinylmethyl pivalate;
5-bromo-2-pyrazinylmethyl pivalate;
5-methoxy-2-pyrazinylmethyl pivalate;
3-amino-2-pyrazinylmethyl pivalate;
5-amino-2-pyrazinylmethyl pivalate;
6-amino-2-pyrazinylmethyl pivalate;
6-methyl-2-pyrazinylmethyl pivalate;
3-methyl-2-pyrazinylmethyl pivalate;
5,6-dimethyl-2-pyrazinylmethyl pivalate;
2-pyrazinylmethyl propionate;
6-methyl-2-pyrazinylmethyl propionate;
5-methyl-2-pyrazinylmethyl propionate; 5,6-dimethyl-2-pyrazinylmethyl propionate;
5-fluoro-2-pyrazinylmethyl propionate;
5-chloro-2-pyrazinylmethyl propionate;
5-bromo-2-pyrazinylmethyl propionate;
5-methoxy-2-pyrazinylmethyl propionate;
3-amino-2-pyrazinylmethyl propionate;
5-amino-2-pyrazinylmethyl propionate;
6-amino-2-pyrazinylmethyl propionate;
2-pyrazinylmethyl acrylate;
5-methyl-2-pyrazinylmethyl acrylate;
6-methyl-2-pyrazinylmethyl acrylate;
3-methyl-2-pyrazinylmethyl acrylate;
5,6-dimethyl-2-pyrazinylmethyl acrylate;
5-fluoro-2-pyrazinylmethyl acrylate;
5-chloro-2-pyrazinylmethyl acrylate;
5-bromo-2-pyrazinylmethyl acrylate;
5-methoxy-2-pyrazinylmethyl acrylate;
5-amino-2-pyrazinylmethyl acrylate;
3-amino-2-pyrazinylmethyl acrylate;
6-amino-2-pyrazinylmethyl acrylate;
2-pyrazinylmethyl-cyclohexylcarboxylate;
[(5-methyl)-2-pyrazinylmethyl]-cyclohexylcarboxylate;
[(6-methyl-2-pyrazinylmethyl]-cyclohexylcarboxylate;
[(3-methyl)-2-pyrazinylmethyl]-cyclohexylcarboxylate;
[(5-fluoro)-2-pyrazinylmethyl]-cyclohexylcarboxylate;
[(5-chloro)-2-pyrazinylmethyl]-cyclohexylcarboxylate;
[(5-bromo)-2-pyrazinylmethyl]-cyclohexylcarboxylate;
[(5-methoxy)-2-pyrazinylmethyl]-cyclohexylcarboxylate;
[(5-amino)-2-pyrazinylmethyl]-cyclohexylcarboxylate;
[(6-amino)-2-pyrazinylmethyl]-cyclohexylcarboxylate;
[(3-amino)-2-pyrazinylmethyl]-cyclohexylcarboxylate.

EXAMPLE 4

(4-oxido-5-methyl)-2-pyrazinylmethyl pivalate

A solution of 5-methyl-pyrazin-2-yl-methyl-trimethylacetate (2.1 g) in a mixture of glacial acetic acid (6 ml) and 30% w/v hydrogen peroxide (4.1 ml) was rapidly heated to 70° C. and maintained at such temperature, with stirring for 12 hours. The solution was concentrated to a small volume and the solid which formed was filtered and crystallized from isopropyl ether, obtaining 1.1 g (50%) of (4-oxido-5-methyl)-2-pyrazinylmethyl pivalate.

The following compounds were similarly obtained:
4-oxido-2-pyrazinylmethyl-pivalate;
(4-oxido-5-fluoro)-2-pyrazinylmethyl-pivalate;
(4-oxido-5-chloro)-2-pyrazinylmethyl-pivalate;
(4-oxido-5-bromo)-2-pyrazinylmethyl-pivalate;
(4-oxido-5-methoxy)-2-pyrazinylmethyl-pivalate;
(4-oxido-5-amino)-2-pyrazinylmethyl-pivalate;
(4-oxido-5-methyl)-2-pyrazinylmethyl-pivalate;
(4-oxido-3-methyl)-2-pyrazinylmethyl-pivalate;
4-oxido-2-pyrazinylmethyl-propionate;
(4-oxido-5-fluoro)-2-pyrazinylmethyl-propionate;
(4-oxido-5-chloro)-2-pyrazinylmethyl-propionate;
(4-oxido-5-bromo)-2-pyrazinylmethyl-propionate;
(4-oxido-5-methoxy)-2-pyrazinylmethyl-propionate;
(4-oxido-5-amino)-2-pyrazinylmethyl-propionate;
(4-oxido-6-methyl)-2-pyrazinylmethyl-propionate;
(4-oxido-3-methyl)-2-pyrazinylmethyl-propionate;
4-oxido-2-pyrazinylmethyl-cyclohexyl-carboxylate;
[(4-oxido-5-fluoro)-2-pyrazinylmethylmethyl]-cyclohexylcarboxylate;
[(4-oxido-5-chloro)-2-pyrazinylmethyl]-cyclohexylcarboxylate;
[(4-oxido-5-bromo)-2-pyrazinylmethyl]-cyclohexylcarboxylate;
[(4-oxido-5-methoxy)-2-pyrazinylmethyl]-cyclohexylcarboxylate;
[(4-oxido-5-amino)-2-pyrazinylmethyl]-cyclohexylcarboxylate;
[(4-oxido-6-methyl)-2-pyrazinylmethyl]-cyclohexylcarboxylate;
[(4-oxido-3-methyl)-2-pyrazinylmethyl]-cyclohexylcarboxylate;

EXAMPLE 5

(4-oxide-5-hydroxy)-2-pyrazinylmethyl-propionate

To a solution of 4-oxide-5-amino-pyrazin-2-yl-methyl-propionate (1.97 g) in 2 M sulphuric acid (15 ml) cooled to approximately 5° C., addition was made of a solution of sodium nitrite (0.83 g) in water (3.5 ml) while the temperature was maintained between 5° C. and 10° C. for another 30 minutes. The reaction mixture was then gradually heated to 50° C. and then again cooled. The solid which formed was filtered and washed on the filter with a small quantity of ice-water, obtaining 1.1 g (55.5%) of (4-oxido-5-hydroxy)-2-pyrazinylmethyl-propionate.

The following compounds were similarly obtained:
(4-oxido-5-hydroxy)-2-pyrazinylmethyl-acrylate;
(4-oxido-5-hydroxy)-2-pyrazinylmethyl-pivalate;
[(4-oxido-5-hydroxy)-2-pyrazinylmethyl]-cyclohexylcarboxylate;
(4-oxido-3-hydroxy)-2-pyrazinylmethyl-acrylate;
(4-oxido-3-hydroxy)-2-pyrazinylmethyl-pivalate;
(4-oxido-3-hydroxy)-2-pyrazinylmethyl-propionate;
(4-oxido-3-hydroxy)-2-pyrazinylmethyl)-cyclohexylcarboxylate;
(4-oxido-6-hydroxy)-2-pyrazinylmethyl-pivalate;
(4-oxido-6-hydroxy)-2-pyrazinylmethyl-propionate;
(4-oxido-6-hydroxy)-2-pyrazinylmethyl-acrylate;
(4-oxido-6-hydroxy)-2-pyrazinylmethyl-cyclohexylcarboxylate.

EXAMPLE 6

2-hydroxymethyl-5-mercapto-pyrazine-4-oxide

To a solution obtained from metallic sodium (0.46 g) and anhydrous ethyl alcohol (25 ml) addition was made of anhydrous dimethylformamide (30 ml). Most of the ethyl alcohol was removed by distillation and the residual solution was saturated with hydrogen sulphide, with subsequent addition of 2-hydroxymethyl-5-bromo-pyrazine-4-oxide (2.05 g). The reaction mixture was maintained at 80° C. for two hours under stirring, the solvent was evaporated and the residue was dissolved in water (10 ml). On acidification of the aqueous solution with glacial acetic acid a precipitate was produced which was treated with 1 N sodium hydroxide without heating; after filtering the insoluble matter, the filtrate was again acidified with acetic acid. By filtration, washing and drying of the precipitate thus caused, there was obtained 0.9 g (58%) of 2-hydroxymethyl-5-mercapto-pyrazine-4-oxide.

The following 5-mercapto derivatives were similarly obtained:
5-mercapto-2-pyrazinylmethyl-propionate;
5-mercapto-2-pyrazinylmethyl-acrylate;
5-mercapto-2-pyrazinylmethyl-pivalate;
5-mercapto-2-pyrazinylmethyl-cyclohexylcarboxylate;
(4-oxido-5-mercapto)-2-pyrazinylmethyl-propionate;
(4-oxido-5-mercapto)-2-pyrazinylmethyl-acrylate;
(4-oxido-5-mercapto)-2-pyrazinylmethyl-pivalate;
(4-oxido-5-mercapto)-2-pyrazinylmethyl-cyclohexylcarboxylate.

EXAMPLE 7

With the usual methods of pharmaceutical technique, preparation was made of capsules having the following composition:

| Composition: | |
|---|---|
| 2-hydroxymethyl-5-methylpyrazine-4-oxide | 200 mg |
| Starch (F.U.) | 40 mg |
| Microcrystalline cellulose | 23 mg |
| Talc | 8 mg |
| Magnesium stearate | 5 mg |

EXAMPLE 8

With the usual methods of pharmaceutical technique, preparation was made of tablets having the following composition:

| Composition: | |
|---|---|
| 2-hydroxymethyl-5-methylpyrazine-4-oxide | 200 mg |
| Microcrystalline cellulose | 50 mg |
| Lactose | 24 mg |
| Starch (F.U.) | 16 mg |
| Magnesium stearate | 12 mg |

We claim:
1. 2-hydroxymethyl-5-methyl-pyrazine-4-oxide or the pharmaceutically acceptable acid addition salts thereof.
2. A compound of the formula

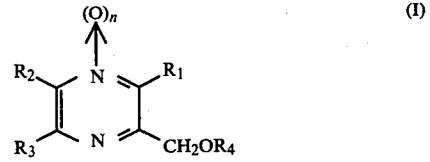

wherein n is 1; $R_1$, $R_3$ and $R_4$ are each hydrogen; and $R_2$ is $C_1$–$C_6$ alkyl, and the pharmaceutically acceptable acid addition salts thereof.

* * * * *